United States Patent [19]

Barbacci

[11] Patent Number: 5,531,741
[45] Date of Patent: Jul. 2, 1996

[54] ILLUMINATED STENTS

[76] Inventor: Josephine A. Barbacci, 3533 Woodmont, Toledo, Ohio 43606

[21] Appl. No.: 292,436

[22] Filed: Aug. 18, 1994

[51] Int. Cl.$^6$ .......................... A61B 17/00; A61M 25/00
[52] U.S. Cl. .............................................. 606/15; 606/153
[58] Field of Search .................................. 606/153, 154, 606/13, 14, 15, 16; 128/4

[56] References Cited

U.S. PATENT DOCUMENTS

| | | |
|---|---|---|
| 3,417,745 | 12/1968 | Sheldon . |
| 4,307,723 | 12/1981 | Finney . |
| 4,610,657 | 9/1986 | Densow . |
| 4,681,104 | 7/1987 | Edelman .................................. 606/15 |
| 4,713,049 | 12/1987 | Carter . |
| 4,738,659 | 4/1988 | Sleiman . |
| 4,906,238 | 3/1990 | Greenfeld et al. ......................... 604/22 |
| 5,159,920 | 11/1992 | Condon et al. ............................. 128/6 |

OTHER PUBLICATIONS

R. Hunter & A. McCartney, "Ureteric Injuries at the Laparoscopic Hysterectomy", Sep. 1993, p. 752.
M. Woodland, "Ureter Injury during Laparoscopy-Assisted Vaginal Hysterectomy...", 1992, p. 756.
V. Gomel & C. James, "Intraoperative Management of Ureteral Injury during Operative Laparoscopy", 1991, p. 416.
R. Evans, J. Hulbert & P. Reddy, "Complications of Laparoscopy", 1992, p. 164.
Neuman, Eidelman, Langer, Golan, Bukovsky, & Capsi, "Iatrogenic Injuries to the Ureter during Gynecologic...", 1991, p. 268.
J. Barone, T. Vates & A. Vasselli, "A Simple Technique for Intraoperatively Stenting a Transected Ureter", 1993, p. 535.
H. Pearse, J. Barry & E. Fuchs, "Intraoperative Consultation for the Ureter", 1985, p. 423.
Grainger, Soderstrom, Schiff, Glickman, DeCherney & Diamond, "Ureteral Injuries at Laparoscopy: Insights...", 1990, p. 839.
Nezhat & Nezhat, "Laparoscopic Repair of Ureter Resected during Operative Laparoscopy", 1992, p. 543.

*Primary Examiner*—Stephen C. Pellegrino
*Assistant Examiner*—Sonya Harris-Ogugua
*Attorney, Agent, or Firm*—Oldham & Oldham Co.

[57] ABSTRACT

An improved radial light emitting ureteral stent is disclosed having an elongated tubular member of substantially uniform outside diameter throughout its length and having a proximal and a distal end, the stent having a central lumen and at least one drainage opening extending through a wall connecting the lumen to the outside, the improvement being the inclusion of at least one fiber optic strand along a length of the tubular member, the strand capable of radially emitting light. The fiber optic strand is connected to a variable voltage source, the strand either being embedded within a wall of the stent or in associative contact with an exterior periphery of the tubular member.

8 Claims, 4 Drawing Sheets

ILLUMINATED STENTS

TECHNICAL FIELD

The invention described herein pertains generally to the field of minimally invasive intraabdominal and retroperitoneal surgery and illuminated stents which are useful therein.

BACKGROUND OF THE INVENTION

Ureteral stents, which function to provide drainage from the kidneys to the bladder, are placed in position in the ureter through an appropriate scope system, typically in retrograde fashion through a cystoscope having a working channel large enough to put the required instruments through, such as stents, guide wires, forceps and the like. Placement of such a large scope into a patient's urethra requires anesthesia and a "cysto-room" environment.

After the scope is placed through the urethra and the tip is within the bladder, the stent is then advanced through the scope, through the bladder and into the ureter. At the point where the stent or part of the stent is in the ureter, the tip of the stent and its full location is no longer visible directly by means of the scope, the scope being too large to itself also be advanced into the ureter. Thus the stent and guide wire must be positioned and progress must be viewed by means of fluoroscopy or ultrasound from outside the patient. Manipulation of the stent and cystoscope while trying to interpret the image given by either fluoroscopy or ultrasound can become quite difficult. In any event, after the stent is in the desired location as detected by a combination of direct vision and fluoroscopy or ultrasound, the stent is left in place by some means of pushing the stent off of its working guide wire or stylet, after which the guide wire or stylet is removed, followed by the removal of the scope from the urethra.

This procedure, though quite routine, is quite cumbersome, as the doctor operating the cystoscope must be sitting low between the patient's legs, and must bend over to view through the cystoscope. Since direct vision is lost anywhere past the bladder, it is not possible for the doctor to actually see where the stent is going, what the condition of the ureter is, what potential obstructions look like, or if a kidney stone is embedded within the walls of the ureter. Thus upon encountering an obstruction, the doctor's options are highly limited, the most obvious option merely being to try to negotiate past the obstruction and proceed with the placement of the stent irrespective of the nature of the obstruction, presence of a kidney stone, etc. For this purpose various forms of stents and guide wires are known.

One form of stent and guide wire system is shown in U.S. Pat. No. 4,307,723. As shown therein, the stent is an elongated, flexible, generally cylindrical member having the proximal end of the stent closed and set in the form of a hook, with the other end also set in the form of a hook with a longitudinal intermediate portion connecting the hooked ends. A stylet is inserted through the open end of the stent and passed through substantially the full length of the stent to straighten both hooks. Also, a stent pusher is threaded over the wire stylet and inserted into the open end of the stent a certain amount to allow the partial withdrawal and redirection of the stent if necessary during the retrograde cystoscope insertion process hereinbefore described. Once the stent is properly positioned, the stylet and stent pusher are removed by withdrawing the stent pusher while holding the wire stylet, causing the stent and stent pusher to disengage, after which the wire stylet and then the stent pusher are withdrawn.

Other stents are of somewhat similar construction to the foregoing though open at the proximal end, with a stent pusher being used to push against the distal end of the stent to encourage the same to move together with (or after) the guide wire into position, after which the stent pusher is used to retain the stent in position as the guide wire is withdrawn, with the stent pusher itself then being withdrawn.

In U.S. Pat. No. 4,610,657, a ureteral stent is disclosed having both ends thereof open, but with the opening at the proximal end being smaller than the opening of the lumen and distal end. In this way, a small guide wire may be inserted through the lumen and through the proximal end to negotiate past obstructions, etc., or alternatively a larger guide wire could be inserted to pass through the lumen, but not through the smaller opening in the proximal end, to act as a stent pusher for stent insertion purposes.

In addition to the foregoing, two-piece guide wires are also known. Such guide wires generally comprise a helically wound flexible outer guide wire portion typically closed at the proximal end, and a solid, more rigid inner guide wire removably positioned within the flexible outer guide wire portion. In this manner, the two guide wire members together may be used as a single guide wire and if necessary, the more rigid central guide wire may be partially withdrawn, making the proximal end of the outer guide wire member more flexible to better manipulate the same past obstructions (See, for instance, U.S. Pat. No. 4,713,049 for a dual guide wire system of this general type).

Obviously, from the foregoing description, cystoscopes for passing through the urethra and into the bladder and having an auxiliary port for insertion of the stent, guide wire, pusher, etc. are well known. In general the auxiliary port of such devices is located to the side of the fiber optic scope, which scope is normally as large as or larger than the stent itself. Thus the overall combination of the fiber optic bundle, cystoscope body, stent, stent pusher, guide wire, etc. is relatively large, requiring that the patient be anesthetized as mentioned before, and being much too large for passage beyond the bladder into the ureter. See for instance, U.S. Pat. No. 4,738,659 disclosing a catheter for use with a cystoscopic lens. Also, of course, such fiber optic scopes are themselves well known in the prior art, such as by way of example as disclosed in U.S. Pat. No. 3,417,745.

In U.S. Pat. No. 5,159,920, a scope and stent system is described, the scope providing visibility not only through the urethra but also through the ureter during the insertion and placement of a ureteral stent. The scope is in the form of a fiber optic bundle having an appropriate provision for lighting and lensing thereof, and preferably having a video camera and monitor responsive to the image formed at the opposite end of the scope for viewing during the scope insertion process. The fiber optic bundle itself is made sufficiently small so that the entire scope may be fabricated with the appropriate dimensions of a typical stent guide wire and made sufficiently flexible for negotiating a tortuous path as required. The scope may be first inserted through an open-ended stent and through the urethra, the bladder and the ureter, and then the stent inserted thereover through the use of an appropriate stent pusher, or alternatively the scope, stent and stent pusher may be advanced together, the scope allowing observation of the procedure and the nature and extent of any obstructions encountered in the insertion process. Alternate embodiments include the provision of an additional working channel within the stent to allow an additional instrument such as a laser lithotriptor to be utilized in conjunction with the placement of the stent, as well as alternate forms of scope systems.

However, in spite of all of the advances made and described above, the ureter remains one of the most frequently damaged structures in intra-abdominal and/or retroperitoneal surgery. It is estimated that in 0.5% to 1–3% of pelvic operations, some type of ureteral injury will occur and this percentage is estimated to increase to 30% for radical procedures for malignant conditions. Operations of this nature may entail dissection, clamping and ligation close to the ureter that is displaced from its normal course, and prone to injury. With the increasing frequency with which more complex gynecological procedures are being performed laparoscopically, this rate is bound to rise. The reasons for this are several fold, but include the variable course of the pathway of the ureter, the fact that each individual is basically "unique" insofar as the precise location of the ureter, and the proximity to vascular structures to be ligated. In females, the proximity of the ureter to the uterosacral ligaments, makes it difficult to delineate these two structures from each other. Additionally, bleeding in the pelvis makes it very difficult to appreciate the fine structures and their anatomic course. In the male pelvis, ureteral injury is usually secondary to either cautery or direct instrument trauma when completing the cephalad extent of a pelvic lymph node dissection. It is at this end-point in the dissection that accumulated blood in the region of the iliac artery and its branches, can easily obscure vision and promote inadvertent ureteral or vessel injury.

Ligation or damage to one or both of the ureters significantly raises morbidity (and even mortality in extreme cases) post-operatively. The problem that exists is that the intraoperative "real-time" techniques that give the surgeon information as to the ureters' course during the procedure or operation are not helpful in the minimally invasive surgery of today.

The problem remains however, that most ureteral injury is not recognized during the surgical intervention. It is reported that less than one-third of the injuries are recognized intraoperatively. The diagnosis is typically made at a later date when the patient presents signs and symptoms suggestive of ureteral injury, e.g., persistent abdominal and/or flank pain, abdominal distention, and fever.

Traditional methods which help delineate the structure are imaging (using material seen on a screen) pre-operatively, intraoperative fluids or dyes concentrated in the urine (to check for leakage if the structure is transected during the procedure), or ureteral stents or intralumen tubes, which are placed preoperatively or intraoperatively to delineate the course of the structure.

Retrograde imaging (cystoscopy involving insertion of an imaging scope via the bladder) requires a skilled operator and is also limited in degree of visualization. Fluids or dyes (such as indigo carmine, sterile milk, methylene blue, etc.) only will show up or "spill" once transection has taken place. If the ureter is kinked or tied off by suture, no dye will spill, but the ureter may be compromised to the same degree. Ureteral stents are placed pre-operatively and can be detected by manual sensation. They are good for "open abdomen" laparotomy procedures where the surgeon can feel the tube. In minimally invasive surgery, the surgeon cannot place his or her hand into the abdomen to feel the stent. Additionally, depending on the overlying pathology (e.g., dense adhesions and thickened scarring, tumor or other pathology), even the sensation of touch does not always clearly allow the surgeon to know the ureter's course with accuracy or surety.

There still exists the need for an illuminated stent that could be used to enhance visualization of this easily damaged structure. By using sight rather than touch sensory feedback, lighted stents could be placed pre-operatively or intraoperatively to aid the surgeon in both open laparotomy and closed abdomen minimally invasive surgical procedures. This would give "real-time" and continuous information to the surgeon as clamps and/or sutures were being placed during the procedure to lessen the likelihood of damage.

SUMMARY OF THE INVENTION

In accordance with the present invention, there is provided an illuminated ureteral stent which replaces one sense (touch) with another (sight) for use in the detection of the path of the ureter within the body.

It is another object of this invention to provide enhanced visualization even in the minimally invasive surgical procedures where instrumentation in the abdomen or pelvis is limited.

It is still another object of this invention to provide a variable intensity light source for the visual detection.

It is yet another object of this invention to provide "real-time" visual feedback to the surgeon intraoperatively.

It is still yet another object of this invention to provide an increased level of safety to surgical procedures requiring the use of stents by reducing the risk of intraoperative damage and postoperative morbidity.

It is a further object of this invention to provide a method of documentation of the surgical procedure wherein the illuminated stent can be seen on the recording medium.

It is a still further object of this invention to provide a light source which can be of varied colors for the illumination.

These and other objects of this invention will be evident when viewed in light of the drawings, detailed description, and appended claims.

DETAILED DESCRIPTION OF THE DRAWINGS

The invention may take physical form in certain parts and arrangements of parts, a preferred embodiment of which will be described in detail in the specification and illustrated in the accompanying drawings which form a part hereof, and wherein.

DETAILED DESCRIPTION OF THE INVENTION

Figure 10:
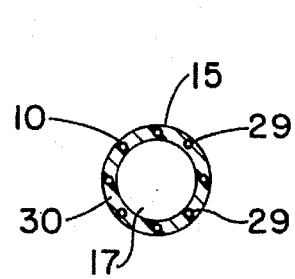
FIG. 10 is an enlarged cross-sectional view of FIG. 1 showing the fiber-optic illuminated strands embedded within the stent.

Referring now to the drawings wherein the showings are for purposes of illustrating the preferred embodiment of the invention only and not for purposes of limiting the same, the figures show an illuminated stent which provides a visual detection means for the pathway of the ureter.

Figure 1:
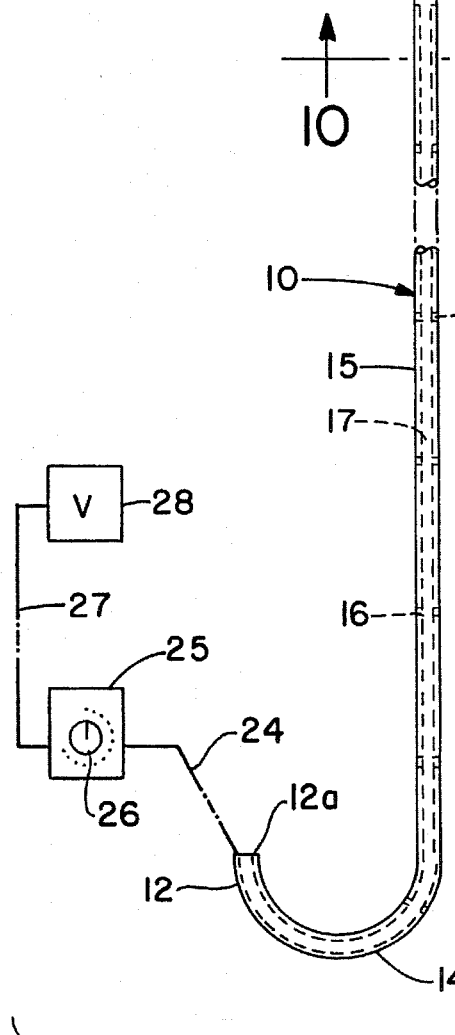
FIG. 1 is an elevational view of the preferred embodiment of the stent, the stent pusher and the guide wires of the present invention.
Figure 2:
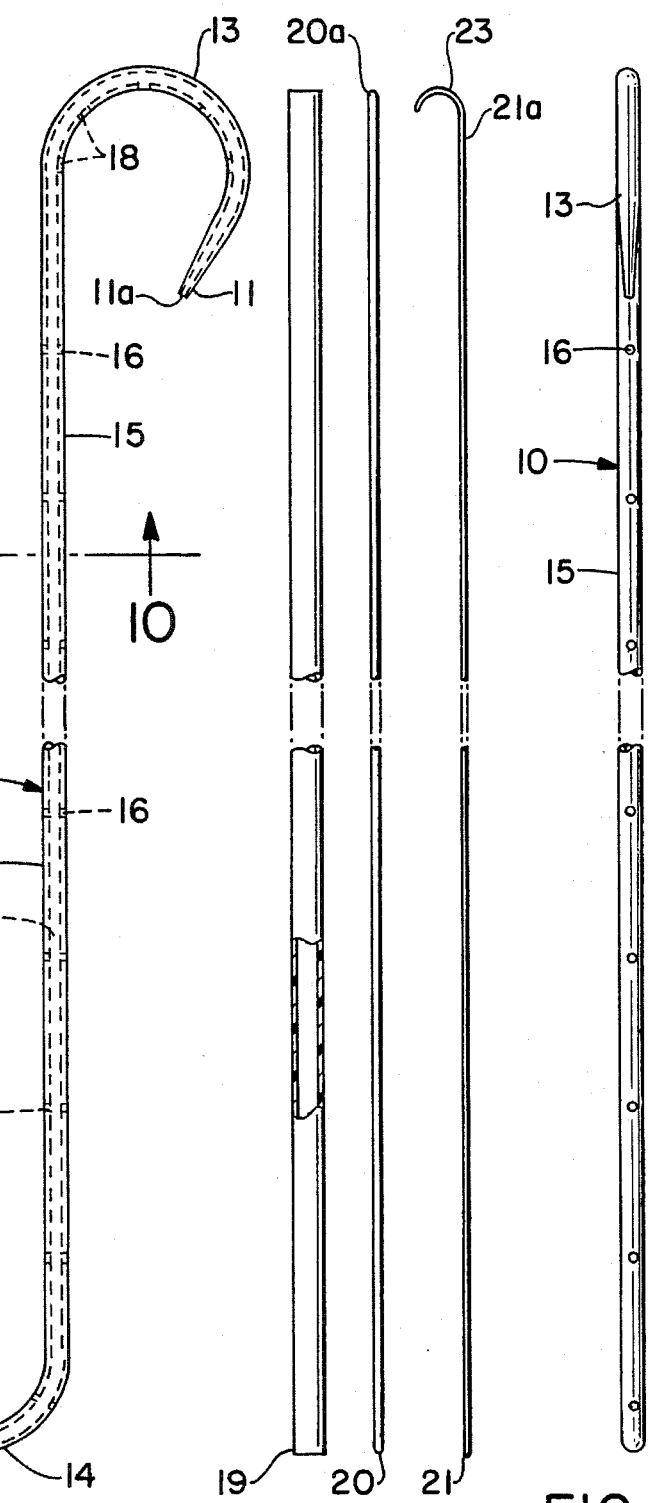
FIG. 2 is a view of the back of the stent of FIG. 1.

In FIG. 1, the stent 10 is seen to be an elongated tubular member having a proximal end 11 and a distal end 12. The portion adjacent to end 11 is formed and set in the shape of a gently curved hook 13. The portion adjacent to end 12 generally being straighter in that it will facilitate removal subsequent to the surgical procedure. In some procedures however, it may be desirable for both of the protions adjacent to each of the ends 11 and 12 to be formed and set in the shape of gently curved hooks, thereby preventing the stent from migrating either upwardly or downwardly once it is in place. A suitable material may be incorporated into the hooks 13 and 14 to make them less flexible and therefore make the stent more resistant to migration. The hooks 13 and 14 extend in opposite directions so that when the stent 10 is used as an indwelling ureteral stent the proximal end 11 can hook into the lower calix or renal pelvis while the distal end 12 curves out into the bladder. This design also prevents the tip of the stent from impinging directly into the bladder mucosa thereby decreasing discomfort and inflammation.

The stent 10 includes a relatively straight intermediate section 15 which extends between the proximal hook 13 and the distal hook 14. The stent 10 is made of a suitable flexible material such as nylon which is soft and stiff enough for the intended purpose and which contains at least one, and preferably a plurality of fiber optic strands 29 within the stent as shown best in FIG. 10. The number of strands is varied and depends upon the amount of desired illumination emanating therefrom. While in a preferred embodiment the strands are embedded within the thickness of the wall cavity of the stent, in some circumstances, they may be attached to the exterior periphery thereof.

The fiber optic strands emanate from the distal end 12 of the stent 10 and are connected via connecting wire 24 to a variable voltage source 25, the voltage of which is adjusted via adjustment means 26. The variable voltage source is connected to a power source 28 via cable 27.

Figure 11:
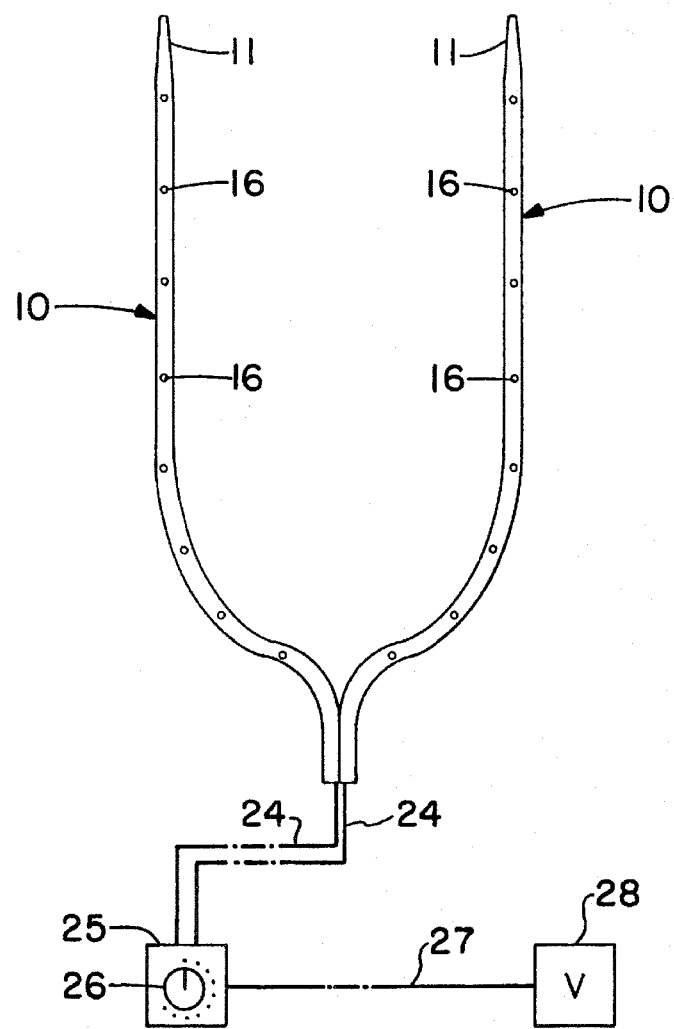
FIG. 11 is a top plan view of a pair of individual stents connected to a variable voltage source.

While the stent 10 has been shown as a single entity, in actual practice, it may be desirable to employ the stents in pairs as shown in FIG. 11 wherein shown in stylized fashion, a pair of stents are shown connected to one variable voltage source 25, which may contain two variable adjustment means 26 (not shown), thereby permitting the operator to control the intensity of each stent individually.

The stent may be supplied in a variety of sizes for pediatric and adult use, such as 5, 6, 7 and 8.5 French sizes in 16, 24, 26, 28 and 30 cm lengths. The listed length of the stent 10 is the length of the section 15 and does not include the hooked or slightly curved ends 13 and 14. This allows the user to radiographically estimate the ureteral length and select the proper stent for passage.

Figure 4:
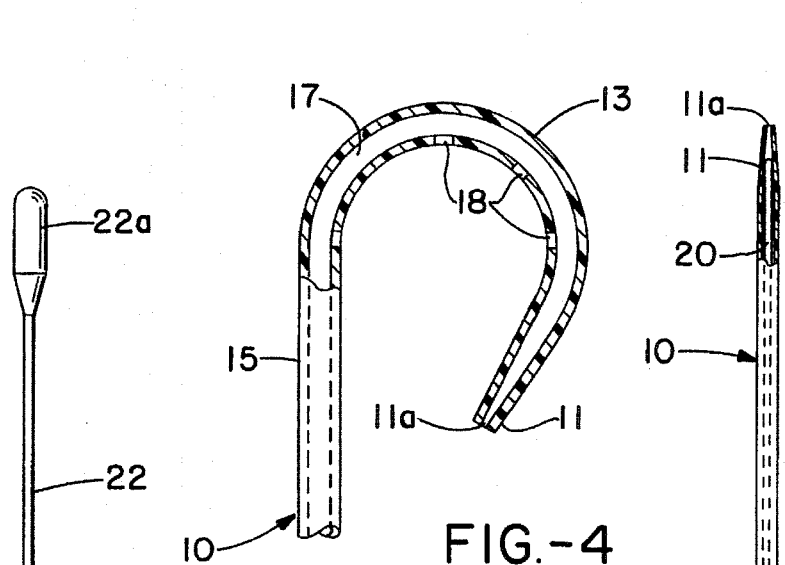
FIG. 4 is a enlarged view partly in section of the proximal end of the stent of FIG. 1.
Figure 5:
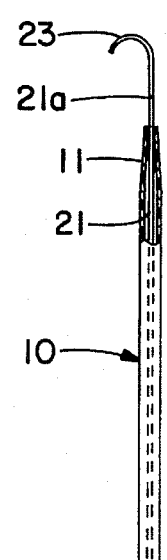
FIG. 5 is an enlarged sectional view of a body portion of the stent of FIG. 1.

Referring now to FIGS. 1, 2, 4 and 5, it can be seen that the stent 10 has radial drainage passage 16 which connect the lumen 17 of the stent 10 to the outside and permit inside/outside drainage. The drainage passages 16 are located about 5 centimeters apart on both sides of the straight section 15. As best seen in FIG. 5, the passages 16 of both sides are preferably aligned, but can be variable in number and position. Returning to FIGS. 1 and 4, it can be seen that there are similar but larger openings 18 in the inside wall of the proximal hook 13.

Figure 3:
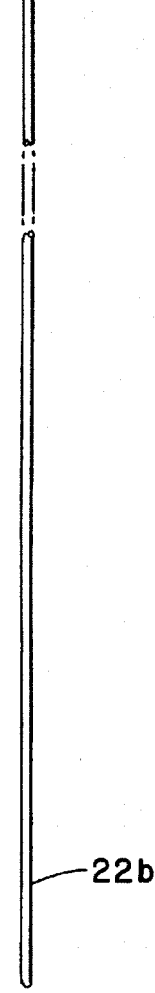
FIG. 3 is an elevational view of a guide wire with an an enlarged proximal end.

Referring again to FIG. 1, there also can be seen a stent pusher 19, a relatively large diameter guide wire 20 which is normally used to position the stent 10 in a body passage, and a smaller diameter guide wire 21 which is used to bypass difficult obstructions and to replace the stent. In FIG. 3, a guide wire 22 is shown which has an enlarged proximal end 22a; it also can be used in the normal placement of the stent 10 and to bypass obstructions.

Figure 7:
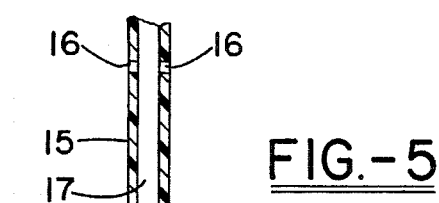
FIG. 7 is an enlarged sectional view of the proximal end of the stent and the guide wire of FIG. 6.
Figure 6:
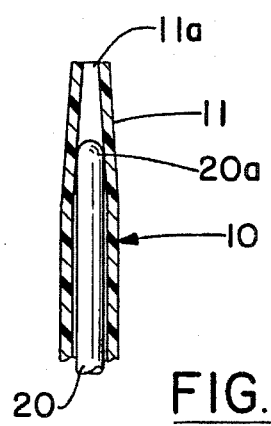
FIG. 6 is an elevational view showing the larger guide wire in the stent and the hooks straightened.

The stent 10 is supplied with both ends 11 and 12 open. As best seen in FIG. 4, the proximal end opening 11a is smaller than the distal end opening 12a or the lumen 17. When normal endoscopic insertion is employed, the relatively large diameter guide wire 20 is introduced into the lumen 17 of the stent 10 to straighten both hooks 13 and 14 as seen in FIG. 6. When this is done the end 20a of the guide wire 20 is prevented from leaving the lumen 17 of the stent 10, as seen in FIG. 7, because of the relatively small proximal opening 11a.

To assist in properly positioning the stent 10, the stent pusher 19 is threaded over the free end of the guide wire 20. If the stent pusher 19 is small enough it can be force fit into the distal opening 12a; this allows for the partial withdrawal and redirection of the stent, if necessary, during standard retrograde catheterization. The stent pusher 19 is then used to advance the stent 10 into position. Once the stent 10 is properly positioned, the guide wire 20 and the stent pusher 19 are removed by withdrawing the stent pusher 19 while holding the guide wire 20 thus causing the stent 10 and stent pusher 19 to separate after which the guide wire 20 and then the stent pusher 19 are withdrawn.

Figure 8:
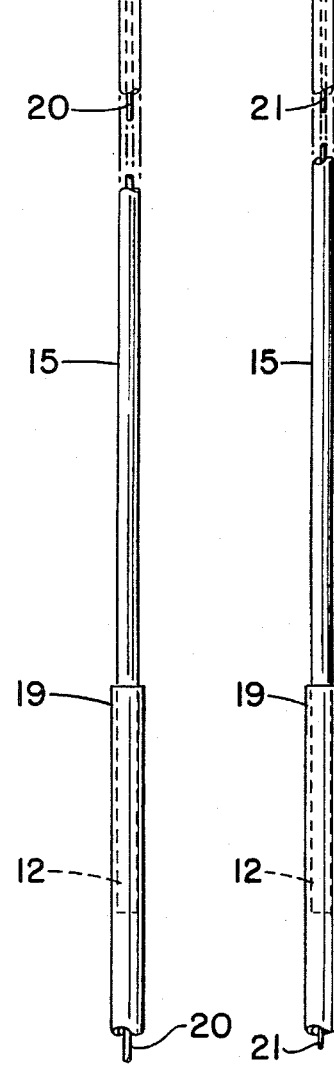
FIG. 8 is an elevational view similar to FIG. 6 but showing the smaller guide wire in the stent.
Figure 9:
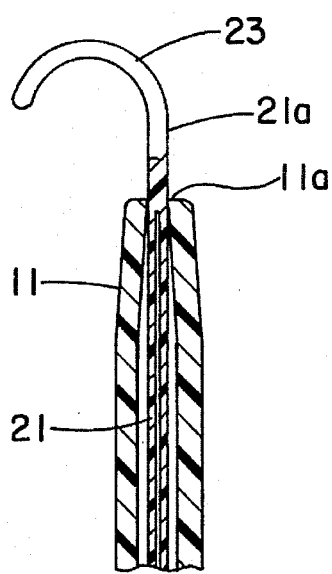
FIG. 9 is an enlarged sectional view of the proximal end of the stent and smaller guide wire of FIG. 8.

When an obstruction in the ureter is encountered that cannot be bypassed by the stent 10 using the normal method of introduction, the stent 10 and guide wire 20 are withdrawn and the stent 10 is threaded on the smaller diameter guide wire 21 which has a forgiving, unreinforced tip 23 on its proximal end 21a (seen best in FIGS. 8 and 9). The forgiving, unreinforced tip 23 minimizes the possibility of damage being caused to the body by the guide wire 21. The tip 23 and proximal end 21a of the guide wire 21 are passed through the proximal opening 11a of the stent and maneuvered past the obstruction in the ureter. When it is known that the tip 23 and the proximal end 21a are safely past the obstruction, the stent 10 is advanced over the guide wire 21 past the obstruction and pushed into place with the stent pusher 19. The guide wire 21 is then withdrawn and the stent pusher 19 is disengaged from the stent 10.

The guide wire 22 can be used in a similar manner to position the stent 10 and to bypass an obstruction. When no difficulty with obstructions is anticipated, the enlarged head 22a of the guide wire 22 is introduced first into the lumen 17 of the stent 10. When difficult obstructions are encountered the opposite end 22b of the guide wire 22 is introduced first into the lumen 17 and the stent is maneuvered past the obstruction in the same manner as described with small guide wire 21.

When it is desired to replace an indwelling stent of the present invention, the radiopaque stent is first cystoscopically visualized and then a foreign body forceps or a retractable type stone basket (neither shown) is used to retract the stent 10 until the distal end 12 can be reached; care, of course, must be taken to not retract the stent 10 past any obstructions in the ureter. Next, the proximal end 21a and tip 23 of the smaller guide wire 21 are threaded through the distal opening 12a into lumen 17 of the stent 10 and advanced to straighten the hooks 13 and if present, 14 (as seen in FIG. 8). The guide wire 21 is further advanced until the proximal end 21a and tip 23 pass through the proximal opening 11a as seen in FIGS. 8 and 9. The stent 10 is then withdrawn without removing the guide wire 21. A new stent is threaded proximal end first over the guide wire 21 and advanced as previously described into the proper position, e.g. into the bladder, through the ureter and into the kidney. When the new stent is properly in place, the guide wire 21 is then withdrawn. The ureteral catheter stent 10 of the present invention is preferably made of nylon which has a durometer between about 70 Shore 'A' and about 55 Shore 'D'. Stents made of this material have been found to be soft enough not to cause undue discomfort to the patient and stiff enough to bypass obstructions in the ureter. However, the stent is not limited to nylon, as other flexible plastic materials such as silicone rubber which possess the desired properties and resist encrustation with urine salts, can also be used.

The stent 10 is preferably formed by extruding a length of tubing of the desired size and durometer. The proximal end 11 of the tubing is then placed in a mold to reduce the size of the opening 11a to less than the diameter of the larger guide wire 20 and the lumen 17. The length of tubing is then placed in a form to shape the hooks 13 and 14. The drainage openings 16 and 18 may be formed at any step of the process by piercing the wall of the tubing with a flattened, sharpened hole cutter of the desired size or by use of a laser or any other conventional means.

The ureteral catheter stent 10 of the present invention may be supplied as a component of a kit for normal insertion and to bypass difficult obstructions or a kit for replacing an indwelling stent. A kit for normal insertion and to bypass difficult ureteral obstructions might contain a stent 10 of the desired size and either the two guide wires 20 and 21 or the combination guide wire 22 (seen only in FIG. 3).

A kit for replacing an indwelling stent would include a replacement stent 10 and a guide wire 21. A stent pusher 19 may be supplied as a component of either of the kits or a satisfactory stent pusher 19 also may be made from a half length of a relatively stiff standard ureteral catheter, preferably 5 French.

In the preferred embodiment, only the proximal end portion of the catheter stent would be in the form of a gently curved hook. However, it is to be understood that the term "hook" is intended to include other functionally equivalent shapes which prevent migration and do not increase the effective outer diameter of the stent, or complicate its method of introduction.

Figure 12:
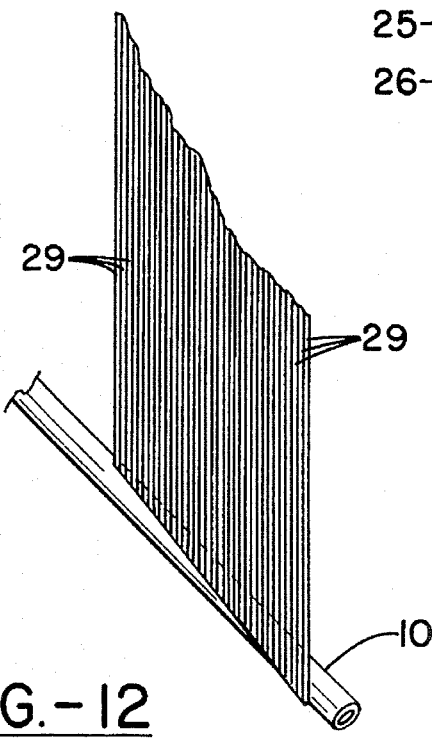
FIG. 12 is an enlarged partial perspective view of a ureteral stent showing a spiral wrap pattern about a stent.
Figure 13:
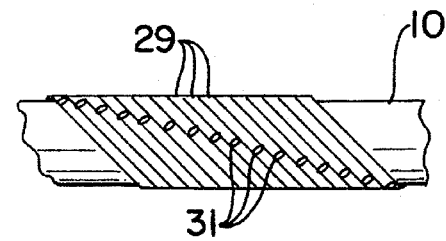
FIG. 13 is an enlarged elevational view showing individual fiber ends within a "wrapping" of fiber optical wire.

FIGS. 12–13 show an alternative embodiment of a ureteral stent 10 over which fiber optic fibers 29 have been wound in a spiral configuration to cover the stent, a series of fiber terminal ends 31 being indicated in FIG. 13. It is of course envisioned that a plurality of fiber optic fiber sheets could be wrapped about a stent, thereby producing a layered product. Depending upon the design, the second layer could be added with a bias in the opposite direction to that of the first layer of the fiber optic sheet.

Figure 14:
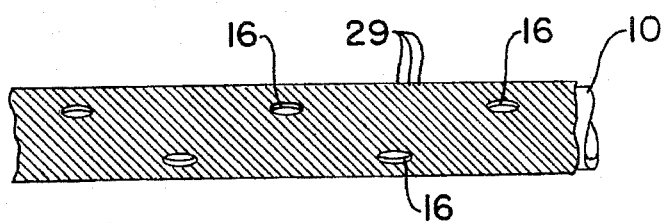
FIG. 14 is an enlarged partial side view of a ureteral stent spiral wrapped with optic fibers into which drainage holes have been provided.
Figure 15:
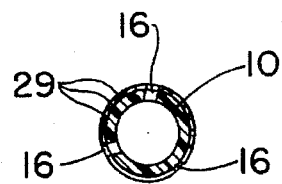
FIG. 15 is a transverse sectional view through the stent shown in FIG. 14.

As best seen in FIGS. 14–15, once the stent has been wrapped with a fiber optic sheet, radial drainage passages 16 are typically drilled or punched into the stent for drainage purposes. It is of course obvious that where a fiber optic strand is broken, the amount of illumination will increase, thereby pin-pointing the location of the drainage holes.

Figure 16:
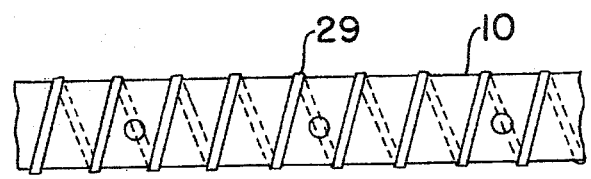
FIG. 16 is an enlarged partial side view of a ureteral stent showing a spiral wrap pattern about a stent with drainage holes.
Figure 17:
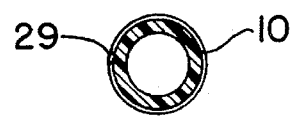
FIG. 17 is a transverse sectional view through the stent of FIG. 16.

While a tightly wrapped sheath of fiber optic fibers has been shown in previous figures, there is no need to limit the invention to such. In fact, as shown in FIGS. 16–17, the fiber optic strands 29 can be spaced and spiral wound around the stent thereby enabling the radial drainage passages 16 to be included in the stent without the need to break any one or several of the fiber optic strands.

Figure 18:
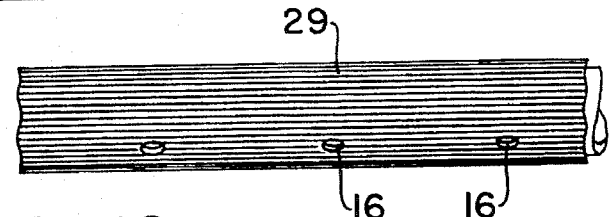
FIG. 18 is an enlarged partial side view of a ureteral stent showing a multi-layered longitudinal wrap pattern about a stent with drainage holes.
Figure 19:
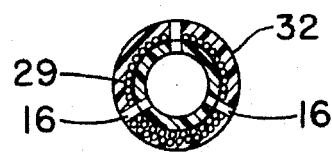
FIG. 19 is a transverse sectional view through the stent of FIG. 18.

As shown in FIGS. 18–19, the wrapping pattern of the fiber optic strands 16 can be along a longitudinal axis of the stent. The spacing between the strands can vary depending upon the degree of illumination required. Greater illumination will require that the spacing between fiber optic strands be minimized, whereas less illumination will permit larger spacing. Additionally, several layers of strands can be positioned around the stent as best seen in FIG. 19. In some instances, a supplemental outer covering 32 may be desired. This coating may be for example, a silicone layer, thereby minimizing the roughness of the exterior surface of the stent, a desirable feature when inserting the stent into easily damaged ureteral walls.

Figure 20:
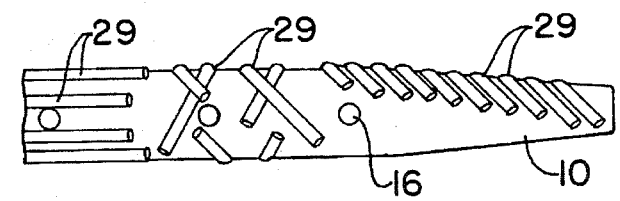
FIG. 20 is an enlarged partial side view of a ureteral stent showing a combination wrap pattern about a stent with drainage holes.
Figure 21:
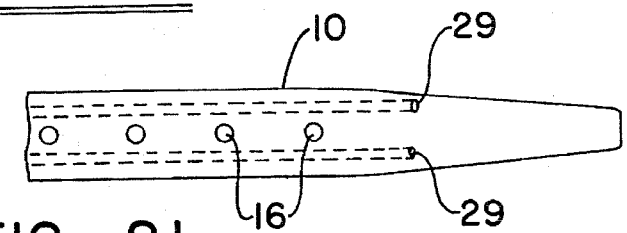
FIG. 21 is an enlarged partial side view of a ureteral stent showing single optical fibers embedded longitudinally within a stent with drainage holes.
Figure 22:
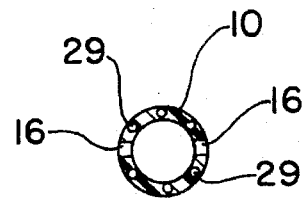
FIG. 22 is a transverse sectional view through the stent of FIG. 21.

In FIG. 20, the ability to combine different fiber optic wrapping patterns is shown, wherein both a longitudinal wrapping pattern is combined with a spiral wrapping pattern. FIGS. 21–22 show a ureteral stent wherein a minimal number of fiber optic strands 29 are embedded within the wall of the stent, with drainage channels interspersed therein.

While it is envisioned that the fiber optic strand will be essentially radially uniform in cross-section, there is no need to limit the application to such. In fact, it is anticipated that non-radially uniform fiber optic strands would function equally well in this intended application.

The best mode for carrying out the invention has been described for the purposes of illustrating the best mode known to the applicant at the time. The invention has been described with reference to preferred and alternate embodiments. Obviously, modifications and alterations will occur to others upon the reading and understanding of the specification. One such modification would be the use of the ureteral stent in, for example, vascular insertions (venous/arterial), and within other hominal organs, for example, fallopian tubes, gastrointestinal tract, etc. It is intended to include all such modifications and alterations insofar as they come within the scope of the appended claims or the equivalents thereof.

What is claimed is:

1. An improved ureteral stent having an elongated tubular member made of a light transmissive material, of substantially uniform outside diameter throughout its length and having a proximal and a distal end, the stent having a central lumen and at least one drainage opening extending through a wall connecting the lumen to the outside, the improvement which comprises said tubular member having a fiber optic means embedded within the tubular member, the means radially emitting light along at least a portion of the stent to provide a visual detection means for the pathway of a ureter.

2. The stent of claim 1 wherein the fiber optic strand is connected to a variable voltage source.

3. The stent of claim 2 which further comprises a light source which can be of varied colors.

4. The stent of claim 1 wherein the tubular member has a lumen which tapers inwardly adjacent the proximal end to terminate in an opening at the proximal end which is smaller in diameter than the central lumen, the opening serving to allow the passage of a thin guide wire to maneuver past an obstacle and also serving to block the exit of a thick insertion wire from the lumen so that the thick insertion wire can be used to push the stent into a desired position in a patient's ureter.

5. An improved ureteral stent comprising:

(a) an elongated tubular member made of a light transmissive material, of substantially uniform outside diameter throughout its length and having a proximal and a distal end, the stent having a central lumen and at least one drainage opening extending through a wall connecting the lumen to the outside; and (b) a fiber optic means embedded within the tubular member radially emitting light along at least a portion of the stent to provide a visual detection means for the pathway of a ureter.

6. The stent of claim 5 wherein the fiber optic strand is connected to a variable voltage source.

7. The stent of claim 6 which further comprises a light source which can be of varied colors.

8. The stent of claim 5 wherein the tubular member has a lumen which tapers inwardly adjacent the proximal end to terminate in an opening at the proximal end which is smaller in diameter than the central lumen, the opening serving to allow the passage of a thin guide wire to maneuver past an obstacle and also serving to block the exit of a thick insertion wire from the lumen so that the thick insertion wire can be used to push the stent into a desired position in a patient's ureter.

* * * * *